United States Patent
Kobayashi et al.

(10) Patent No.: US 9,724,448 B2
(45) Date of Patent: Aug. 8, 2017

(54) MATERIALS FOR GASTROINTESTINAL OBSTRUCTION PREVENTION

(71) Applicant: 3-D MATRIX, LTD., Tokyo (JP)

(72) Inventors: Satoru Kobayashi, Kanagawa (JP); Toshio Uraoka, Tokyo (JP); Naohisa Yahagi, Tokyo (JP)

(73) Assignee: 3-D MATRIX, LTD., Tokyo (JP)

( * ) Notice: Subject to any disclaimer, the term of this patent is extended or adjusted under 35 U.S.C. 154(b) by 0 days.

(21) Appl. No.: 14/775,904

(22) PCT Filed: Mar. 13, 2014

(86) PCT No.: PCT/IB2014/059748
§ 371 (c)(1),
(2) Date: Sep. 14, 2015

(87) PCT Pub. No.: WO2014/141143
PCT Pub. Date: Sep. 18, 2014

(65) Prior Publication Data
US 2016/0000966 A1    Jan. 7, 2016

Related U.S. Application Data

(60) Provisional application No. 61/785,582, filed on Mar. 14, 2013.

(51) Int. Cl.
*A61L 27/22* (2006.01)
*A61L 31/04* (2006.01)
*A61L 27/50* (2006.01)
*A61L 27/52* (2006.01)
*A61L 27/54* (2006.01)

(52) U.S. Cl.
CPC .............. *A61L 27/227* (2013.01); *A61L 27/50* (2013.01); *A61L 27/52* (2013.01); *A61L 27/54* (2013.01); *A61L 31/047* (2013.01); *A61L 2400/06* (2013.01); *A61L 2430/22* (2013.01)

(58) Field of Classification Search
None
See application file for complete search history.

(56) References Cited

U.S. PATENT DOCUMENTS

2008/0032934 A1    2/2008    Ellis-Behnke et al.
2011/0201541 A1    8/2011    Takamura et al.

FOREIGN PATENT DOCUMENTS

EP        2345433 A1    7/2011
WO    2008039483 A2    4/2008

OTHER PUBLICATIONS

International Search Report and Written Opinion dated Jun. 13, 2014 for Application No. PCT/IB2014/059748.

*Primary Examiner* — Christina Bradley
(74) *Attorney, Agent, or Firm* — Lando & Anastasi, LLP

(57) ABSTRACT

Materials and methods for preventing gastrointestinal obstruction are provided. A peptide comprising between about 7 amino acids and about 32 amino acids in a solution may be introduced to a target site. The peptide may undergo self-organization under physiological conditions and/or in the presence of a cation.

54 Claims, 4 Drawing Sheets

MATERIALS FOR GASTROINTESTINAL OBSTRUCTION PREVENTION

CROSS-REFERENCE TO RELATED APPLICATIONS

This application is a U.S. national stage application and claims the benefit under 35U.S.C. §371 of PCT/IB2014/059748, titled MATERIALS FOR GASTROINTESTINAL OBSTRUCTION PREVENTION, filed Mar. 13, 2014, which claims priority to United States Provisional Application Ser. No. 61/785,582, titled, MATERIALS FOR GASTROINTESTINAL OBSTRUCTION PREVENTION, filed Mar. 14, 2013, which contents are hereby incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created Mar. 12, 2014, is named T2071-7008WO_SL.txt and is 29,161 bytes in size.

FIELD OF THE DISCLOSURE

This disclosure generally relates to materials and methods that may be used in medical, research, and industrial applications. More particularly, this disclosure relates to materials and methods that may be used for gastrointestinal obstruction prevention, including membranes, hydrogels, compositions, and solutions that may be used to treat gastric ESD-induced ulcers.

SUMMARY

In accordance with one or more aspects, a method for preventing gastrointestinal obstruction in a subject is provided. The method may comprise introducing a catheter into a gastrointestinal tract. The method may also comprise positioning an end of the catheter in a target area of the gastrointestinal tract in which at least a partial prevention of gastrointestinal obstruction is desired. The method may further comprise administering through the catheter a solution comprising a self-assembling peptide comprising between about 7 amino acids and about 32 amino acids in an effective amount and in an effective concentration to form a hydrogel under conditions of the gastrointestinal tract to provide prevention of gastrointestinal obstruction. The method may further comprise removing the catheter from the gastrointestinal tract.

In accordance with one or more aspects, a kit for preventing a gastrointestinal obstruction in a subject is provided. The kit may comprise a solution comprising a self-assembling peptide comprising between about 7 amino acids and about 32 amino acids in an effective amount and in an effective concentration to form a hydrogel under physiological conditions to allow prevention of the gastrointestinal obstruction. The kit may also provide instructions for administering the solution to a target area of the gastrointestinal tract of the subject.

In accordance with one or more aspects, a method of facilitating prevention of a gastrointestinal obstruction in a subject may comprise providing a solution comprising a peptide comprising between about 7 amino acids and about 32 amino acids in an effective amount and in an effective concentration to form a hydrogel under physiological conditions to allow prevention of the gastrointestinal obstruction. The method of facilitating may also comprise providing instructions for administering the solution to a target area of the gastrointestinal tract through introduction of the solution through a catheter positioned in the gastrointestinal tract.

In accordance with one or more aspects, a macroscopic scaffold consisting essentially of a plurality of self-assembling peptides is provided. Each of the self-assembling peptides comprises between about 7 amino acids and about 32 amino acids in an effective amount that is capable of being positioned within a lesion area of a gastrointestinal tract to promote healing and to prevent a gastrointestinal obstruction.

BRIEF DESCRIPTION OF THE DRAWING

The accompanying drawings are not intended to be drawn to scale. For purposes of clarity, not every component may be labeled.

In the drawings.

DETAILED DESCRIPTION

Figure 1A:
FIG. 1A is an image of an ulcer prior to endoscopic submucosal dissection (ESD), in accordance with some embodiments.

Materials and methods of the present disclosure may prevent gastrointestinal obstruction.

Endoscopic mucosal resection (EMR) and endoscopic submucosal dissection (ESD) are primary surgical options for resection of lesion sites such as polyps and cancerous tumors in a digestive system or gastrointestinal tract. EMR and ESD are both minimally invasive surgeries. ESD can generally dissect wider areas of a lesion site than EMR. ESD therefore may cause obstructions due to scar contraction/shrinking during the healing process more often than EMR. However, both EMR and ESD procedures may cause lesions that induce post-surgical gastrointestinal obstruction during the course of healing. One form of gastrointestinal obstruction may be a stenosis in the gastrointestinal tract during the course of healing. By stenosis it is meant a narrowing in a tubular organ or structure, such as the gastrointestinal tract, which may lead to a partial or full obstruction in the gastrointestinal tract.

Success of EMD and ESD may require reducing relatively high post-procedure bleeding rates. These rates may be approximately 1 percent for the esophagus, approximately 5 percent for the stomach, and approximately 2 percent for the colorectum. Present treatments for gastric ESD-induced ulcers may include being treated with a proton pump inhibitor for at least 8 weeks after the ESD procedure.

Subjects may typically need to undergo several treatments of balloon dilatation and local steroid injection leading to a significant drop in quality of life. There are currently no options for preventing obstructions, or stenosis, due to scar contraction during its healing process.

The present disclosure provides for materials and methods of preventing or reducing an obstruction, such as a stenosis, in the gastrointestinal tract. The gastrointestinal tract may include any one or more of mouth, throat, esophagus, stomach, small intestine, large intestine or colon, rectum, or colorectum, referred to as the distal portion of the colon and rectum.

The present disclosure also provides for materials and methods of preventing or reducing an obstruction in the gastrointestinal tract. "Preventing" may include complete prevention of a gastrointestinal tract in that a wound, lesion, or target area, may return to a pre-operative state, or in which the wound, lesion, or target area may return to a state prior to the development of a polyp, tumor, or other tissue that may require removal, which may be referred to as a "normal" state. Preventing may include at least partially preventing or at least partially reducing, which may include returning to a state that allows at least some relief of an obstruction of the gastrointestinal tract that returns the wound, lesion, or target area to a lesser than normal state.

The materials and methods may comprise preventing or reducing a gastrointestinal obstruction in the gastrointestinal tract in a subject. As used herein, the term "subject" is intended to include human and non-human animals, for example, vertebrates, large animals, and primates. In certain embodiments, the subject is a mammalian subject, and in particular embodiments, the subject is a human subject. Although applications with humans are clearly foreseen, veterinary applications, for example, with non-human animals, are also envisaged herein. The term "non-human animals" of the invention includes all vertebrates, for example, non-mammals (such as birds, for example, chickens; amphibians; reptiles) and mammals, such as non-human primates, domesticated, and agriculturally useful animals, for example, sheep, dog, cat, cow, pig, rat, among others.

The prevention or reduction of obstruction may be partial or complete. The materials and methods may include administration, application, or injection of a self-assembling peptide, or a solution comprising a self-assembling peptide, or a composition comprising a self-assembling peptide, to a predetermined or desired target area.

The term "self-assembling peptide" may refer to a peptide that may exhibit a beta-sheet structure in aqueous solution in the presence of specific conditions to induce the beta-sheet structure. These specific conditions may include increasing the pH of a self-assembling peptide solution. The increase in pH may be an increase in pH to a physiological pH. The specific conditions may also include adding a cation, such as a monovalent cation, to a self-assembling peptide solution. The specific conditions may include conditions related to a gastrointestinal tract.

The self-assembling peptide may be an amphiphilic self-assembling peptide. By "amphiphilic" it is meant that the peptide comprises hydrophobic portions and hydrophilic portions. In some embodiments, an amphiphilic peptide may comprise, consist essentially of, or consist of alternating hydrophobic amino acids and hydrophilic amino acids. By alternating, it is meant to include a series of three or more amino acids that alternate between a hydrophobic amino acid and a hydrophilic amino acid, and it need not include each and every amino acid in the peptide sequence alternating between a hydrophobic and a hydrophilic amino acid. The self-assembling peptide, also referred to herein as "peptide" may be administered to the pre-determined or desired target area in the form of a self-assembling peptide solution, composition, hydrogel, membrane, scaffold or other form. The hydrogel may also be referred to as a membrane or scaffold throughout this disclosure. The pre-determined or desired target area may be at or near the location of an ESD or EMR, or other resection or surgical removal of tissue in the gastrointestinal tract. The pre-determined or desired target area may be established based on the site of a polyp, tumor, such as a cancerous tumor, or other area that may have undergone a surgical procedure, or an unintentional or intentional trauma.

The self-assembling peptide solution may be an aqueous self-assembling peptide solution. The self-assembling peptide may be administered, applied, or injected in a solution that is substantially cell-free, or free of cells. In certain embodiments, the self-assembling peptide may be administered, applied, or injected in a solution that is cell-free or free of cells.

The self-assembling peptide may also be administered, applied, or injected in a solution that is substantially drug-free or free of drugs. In certain embodiments, the self-assembling peptide may be administered, applied, or injected in a solution that is drug-free or free of drugs. In certain other embodiments, the self-assembling peptide may be administered, applied, or injected in a solution that is substantially cell-free and substantially drug-free. In still further certain other embodiments, the self-assembling peptide may be administered, applied, or injected in a solution that is cell-free and drug free.

The self-assembling peptide solution may comprise, consist of, or consist essentially of the self-assembling peptide. The self-assembling peptide may be in a modified or unmodified form. By modified, it is meant that the self-assembling peptide may have one or more domains that comprise one or more amino acids that, when provided in solution by itself, would not self-assemble. By unmodified, it is meant that the self-assembling peptide may not have any other domains other than those that provide for self-assembly of the peptide. That is, an unmodified peptide consists of alternating hydrophobic and hydrophilic amino acids that may self-assemble into a beta-sheet, and a macroscopic structure, such as a hydrogel.

Administration of a solution may comprise, consist of, or consist essentially of administration of a solution comprising, consisting of, or consisting essentially of a self-assembling peptide comprising, consisting of, or consisting essentially of between about 7 amino acids and about 32 amino acids. Other peptides that do not comprise, consist of, or consist essentially of between about 7 amino acids and about 32 amino acids may be contemplated by this disclosure.

By alternating, it is meant to include a series of three or more amino acids that alternate between a hydrophobic amino acid and a hydrophilic amino acid, and it need not include each and every amino acid in the peptide sequence alternating between a hydrophobic and a hydrophilic amino acid.

The materials and methods may comprise administering a self-assembling peptide to a predetermined or desired target. The peptide may be administered as a hydrogel or form a hydrogel upon administration. A hydrogel is a term that may refer to a colloidal gel that is dispersed in water. The hydrogel may also be referred to as a membrane or scaffold throughout this disclosure. The systems and methods may also comprise applying a self-assembling peptide to a predetermined or desired target as a solution such as an aqueous peptide solution.

The term "administering," is intended to include, but is not limited to, applying, introducing or injecting the self-assembling peptide, in one or more of various forms including, but not limited to, by itself, by way of solution, such as an aqueous solution, or by way of a composition, hydrogel, or scaffold, with or without additional components.

The method may comprise introducing a delivery device at or near a predetermined or desired target area of a subject. The method may comprise introducing a delivery device comprising at least one of a syringe, pipette, tube, catheter, syringe catheter, or other needle-based device to the predetermined or desired target area of a subject. The self-assembling peptide may be administered by way of a syringe, pipette, tube, catheter, syringe catheter, or other needle-based device to the predetermined or desired target area of a subject. The gauge of the syringe needle may be selected to provide an adequate flow of a composition, a solution, a hydrogel, or a liquid from the syringe to the target area. This may be based in some embodiments on at least one of the amount of self-assembling peptide in a composition, peptide solution, or a hydrogel being administered, the concentration of the peptide solution, in the composition, or the hydrogel, and the viscosity of the peptide solution, composition, or hydrogel. The delivery device may be a conventional device or designed to accomplish at least one of to reach a specific target area, achieve a specific dosing regime, deliver a specific target volume, amount, or concentration, and deliver accurately to a target area.

The method of preventing or reducing a gastrointestinal obstruction may comprise introducing a catheter into the subject and positioning an end of the catheter in a predetermined or target area, such as a portion of the gastrointestinal tract. The self-assembling peptide may be administered by way of a catheter to the target area in which at least a partial prevention or reduction in obstruction of the gastrointestinal tract is desired. The use of a catheter may provide a more selective administration of the peptide to provide for a more accurate delivery to the target area. Selective administration of the peptide may allow for enhanced and more targeted delivery of the peptide solution, composition, or hydrogel such that prevention or reduction in a gastrointestinal obstruction or stenosis is successful and positioned in the desired location in an accurate manner. The selective administration may provide enhanced, targeted delivery that markedly improves the positioning and effectiveness of the treatment over use of a syringe or other delivery device. Delivery devices that may be used in the systems, methods, and kits of the disclosure may include a syringe, pipette, tube, catheter, syringe catheter, other needle-based device, tube or catheter.

Use of the catheter may include use of accompanying devices, such as a guidewire used to guide the catheter into position, or an endoscope that may allow proper placement of the catheter and visualization of the target area, and/or the path to the target area. The endoscope may be a tube that may comprise at least one of a light and a camera or other visualization device to allow images of the subject's body to be viewed. The guidewire or endoscope may be introduced into the subject by way of the gastrointestinal tract. For example, by way of the mouth, throat, esophagus, stomach, small intestine, large intestine or colon, or rectum. The endoscope may be introduced to the gastrointestinal tract prior to the introducing the catheter to the tract.

The use of the delivery device, such as a syringe, pipette, tube, catheter, syringe catheter, other needle-based device, catheter, or endoscope may require determining the diameter or size of the opening or tract in which there is a target area, such that at least a portion of the syringe, pipette, tube, syringe catheter, other needle-type device, catheter, or endoscope may enter the opening or tract to administer the peptide, peptide solution, composition, or hydrogel to the target area.

In certain embodiments, the hydrogel may be formed in vitro and administered to the desired location in vivo. In certain examples, this location may be the area in which it is desired to prevent or reduce an obstruction. In other examples, this location may be upstream, downstream of the area, or substantially near the area. It may be desired to allow a migration of the hydrogel to the area in which it is desired to prevent or reduce an obstruction or prevent or reduce stenosis. Alternatively, another procedure may position the hydrogel in the area in which it is desired. The desired location or target area may be at least a portion of an area in which tissue was removed, for example, in or around areas in which a cancerous or precancerous tissue was removed, in which one or more tumors was removed, or in which a biopsy was taken. The desired location or target area may be an ESD or ERD induced ulcer or lesion.

In certain aspects of the disclosure, the hydrogel may be formed in vivo. A solution comprising the self-assembling peptide, such as an aqueous solution, may be inserted to an in vivo location or area of a subject to prevent or reduce an obstruction or prevent or reduce a stenosis at that location. In certain examples, the hydrogel may be formed in vivo at one location, and allowed to migrate to the area in which it is desired to prevent or reduce an obstruction or prevent or reduce a stenosis. Alternatively, another procedure may place the hydrogel in the area in which it is desired to prevent or reduce an obstruction or prevent or reduce a stenosis. The peptides of the present disclosure may be in the form of a powder, a solution, a gel, or the like. Since the self-assembling peptide gels in response to changes in solution pH and salt concentration, it can be distributed as a liquid that gels upon contact with a subject during application or administration.

In certain environments, the peptide solution may be a weak hydrogel and, as a result, it may be administered by way of a delivery device as described herein.

In accordance with one or more embodiments, self-assembling peptides may prevent gastrointestinal obstruction. In at least some embodiments, self-assembling peptides may facilitate mucosal epithelium formation to prevent or reduce post-operative scar formation. The prevention or reduction in post-operative scar formation provides, at least in part, for the prevention or reduction in gastrointestinal obstruction or stenosis. In certain embodiments, this may be because the hydrogel, once in place, provides a scaffold to allow for an infiltration of cells that promote healing of the target area.

Administration of the self-assembling peptides into the mucous membrane subcutaneous layer may cause a lesion to float up away from the fixed muscle layer, and to then be detached by use of high frequency. A hemostatic effect may also be obtained at the time of lesion resection, enabling reducing of the degree of surgery difficulty and risk.

In accordance with one or more embodiments, a macroscopic scaffold is provided. The macroscopic scaffold may comprise, consist essentially of, or consist of a plurality of self-assembling peptides, each of which comprises, consists essentially of, or consists of between about 7 amino acids and about 32 amino acids in an effective amount that is capable of being positioned within a lesion area of a gastrointestinal tract to promote healing and to prevent a gastrointestinal obstruction.

In accordance with some embodiments, the self-assembling peptides may be amphiphilic, alternating between hydrophobic amino acids and hydrophilic amino acids. In accordance with one or more embodiments, a subject may be evaluated to determine a need for preventing gastrointestinal obstruction or stenosis. Once the evaluation has been completed, a peptide solution to administer to the subject may be prepared.

In some embodiments, a biologically active agent may be used with the materials and methods of the present disclosure. A biologically active agent may comprise a compound, including a peptide, DNA sequence, chemical compound, or inorganic or organic compound that may impart some activity, regulation, modulation, or adjustment of a condition or other activity in a subject or in a laboratory setting. The biologically active agent may interact with another component to provide such activity. The biologically active agent may be referred to as a drug in accordance with some embodiments herein. In certain embodiments, one or more biologically active agents may be gradually released to the outside of the peptide system. For example, the one or more biologically active agents may be gradually released from the hydrogel. Both in vitro and in vivo testing has demonstrated this gradual release of a biologically active agent. The biologically active agent may be added to the peptide solution prior to administering to a subject, or may be administered separately from the solution to the subject.

This disclosure relates to aqueous solutions, hydrogels, scaffolds, and membranes comprising self-assembling peptides, sometimes referred to as self-assembling oligopeptides. The peptides may be comprised of a peptide having about 6 to about 200 amino acid residues. The self-assembling peptides may exhibit a beta-sheet structure in aqueous solution in the presence of physiological pH and/or a cation, such as a monovalent cation, or other conditions applicable to the gastrointestinal tract. The peptides may be amphiphilic and alternate between a hydrophobic amino acid and a hydrophilic amino acid. In certain embodiments, the peptide may comprise a first portion that may be amphiphilic, alternating between a hydrophobic amino acid and a hydrophilic amino acid, and another portion or region that is not amphiphilic.

The peptides may be generally stable in aqueous solutions and self-assemble into large, macroscopic structures, scaffolds, or matrices when exposed to physiological conditions, neutral pH, or physiological levels of salt. Once the hydrogel is formed it may not decompose, or may decompose or biodegrade after a period of time. The rate of decomposition may be based at least in part on at least one of the amino acid sequence and conditions of its surroundings.

By "macroscopic" it is meant as having dimensions large enough to be visible under magnification of 10-fold or less. In preferred embodiments, a macroscopic structure is visible to the naked eye. A macroscopic structure may be transparent and may be two-dimensional, or three-dimensional. Typically each dimension is at least 10 μm, in size. In certain embodiments, at least two dimensions are at least 100 μm, or at least 1000 μm in size. Frequently at least two dimensions are at least 1-10 mm in size, 10-100 mm in size, or more.

In certain embodiments, the size of the filaments may be about 10 nanometers (nm) to about 20 nm. The interfilament distance may be about 50 nm to about 80 nm.

"Physiological conditions" may occur in nature for a particular organism, cell system, or subject which may be in contrast to artificial laboratory conditions. The conditions may comprise one or more properties such as one or more particular properties or one or more ranges of properties. For example, the physiological conditions may include a temperature or range of temperatures, a pH or range of pH's, a pressure or range of pressures, and one or more concentrations of particular compounds, salts, and other components. For example, in some examples, the physiological conditions may include a temperature in a range of about 20 to about 40 degrees Celsius. In some examples, the atmospheric pressure may be about 1 atm. The pH may be in the range of a neutral pH. For example, the pH may be in a range of about 6 to about 8. The physiological conditions may include cations such as monovalent metal cations that may induce membrane or hydrogel formation. These may include sodium chloride (NaCl). The physiological conditions may also include a glucose concentration, sucrose concentration, or other sugar concentration, of between about 1 mM and about 20 mM. The physiological conditions may include the local conditions of the mouth, throat, esophagus, stomach, small intestine, large intestine, and rectum.

In some embodiments, the self-assembling peptides may be peptides of between about 6 amino acids and about 200 amino acids. In certain embodiments, the self-assembling peptides may be peptides of at least about 7 amino acids. In certain embodiments, the self-assembling peptides may be peptides of between about 7 amino acids and about 32 amino acids. In certain further embodiments, the self-assembling peptides may be peptides of between about 7 amino acids and about 17 amino acids. In certain other examples, the self-assembling peptides may be peptides of at least 8 amino acids, at least about 12 amino acids, or at least about 16 amino acids.

The peptides may also be complementary and structurally compatible. Complementary refers to the ability of the peptides to interact through ionized pairs and/or hydrogen bonds which form between their hydrophilic side-chains, and structurally compatible refers to the ability of complementary peptides to maintain a constant distance between their peptide backbones. Peptides having these properties participate in intermolecular interactions which result in the formation and stabilization of beta-sheets at the secondary structure level and interwoven filaments at the tertiary structure level.

Both homogeneous and heterogeneous mixtures of peptides characterized by the above-mentioned properties may form stable macroscopic membranes, filaments, and hydrogels. Peptides which are self-complementary and self-compatible may form membranes, filaments, and hydrogels in a homogeneous mixture. Heterogeneous peptides, including those which cannot form membranes, filaments, and hydrogels in homogeneous solutions, which are complementary and/or structurally compatible with each other may also self-assemble into macroscopic membranes, filaments, and hydrogels.

The membranes, filaments, and hydrogels may be non-cytotoxic. The hydrogels of the present disclosure may be digested and metabolized in a subject. The hydrogels may be biodegraded in 30 days or less. They have a simple composition, are permeable, and are easy and relatively inexpensive to produce in large quantities. The membranes and filaments, hydrogels or scaffolds may also be produced and stored in a sterile condition. The optimal lengths for membrane formation may vary with at least one of the amino acid composition, solution conditions, and conditions at the target site.

In certain embodiments, a method of preventing gastrointestinal obstruction in a subject is provided. The method may comprise introducing a catheter in a target area of the gastrointestinal tract in which at least a partial prevention of gastrointestinal obstruction is desired. The method may further comprise administering through the catheter a solution comprising a self-assembling peptide comprising between about 7 amino acids and about 32 amino acids in an effective amount and in an effective concentration to form a hydrogel under conditions of the gastrointestinal tract to provide a least partial prevention of gastrointestinal obstruction. The method may further comprise removing the catheter from the gastrointestinal tract.

The method may further comprise visualizing a region or target area comprising at least a portion of the gastrointestinal tract. Visualizing the region or target area may comprise visualizing the region or target area during at least one of identifying the target area of the gastrointestinal tract, introducing the catheter, positioning the end of the catheter in the target area, administering the solution, removing the catheter, and monitoring the gastrointestinal tract after removing the catheter. Visualizing the region or target area may provide for selective administration of the solution to the gastrointestinal tract. Visualizing may occur at any time before, during, and after the administration of the solution. Visualization may occur, for example, at a time period of at least one of about one week subsequent to administration, about four weeks subsequent to administration and about eight weeks subsequent to administration.

The solution to be administered may consist essentially of, or consist of, a self-assembling peptide comprising at least about 7 amino acids. The solution to be administered may consist essentially of, or consist of, a self-assembling peptide comprising between about 7 amino acids and about 32 amino acids. The peptide may be amphiphilic and at least a portion of the peptide may alternate between a hydrophobic amino acid and a hydrophilic amino acid.

The methods of facilitating of the present disclosure may comprise providing instructions for administering through a catheter a solution comprising a self-assembling peptide comprising between about 7 amino acids and about 32 amino acids in an effective amount and in an effective concentration to form a hydrogel under gastrointestinal tract conditions to at least partially prevent or reduce a gastrointestinal obstruction. The peptide may be amphiphilic and at least a portion of the peptide may alternate between a hydrophobic amino acid and a hydrophilic amino acid.

The methods of facilitating may comprise providing the solution comprising a self-assembling peptide comprising between about 7 amino acids and about 32 amino acids in an effective amount and in an effective concentration to form a hydrogel under physiological conditions to at least partially prevent or reduce a gastrointestinal obstruction. The peptide may be amphiphilic and at least a portion of the peptide may alternate between a hydrophobic amino acid and a hydrophilic amino acid.

The methods of facilitating may comprise providing instructions to visualize a region or target area comprising at least a portion of the gastrointestinal tract. The method may comprise providing instructions to visualize the target area or region during at least one of identifying the target area of the gastrointestinal tract, introducing a catheter, positioning an end of the catheter in the target area, administering the solution, removing the catheter from the gastrointestinal tract, and monitoring the gastrointestinal tract after removing the catheter. The methods of facilitating may comprise providing instructions to visualize the region or target area by imaging using an endoscope. The method may comprise providing instructions to visualize the target area in a time period about one week, about four weeks, or about eight weeks subsequent to the administration. Instructions may be provided to monitor the area at the target area or surrounding the target area. Instructions may be provided to use the methods of the present disclosure after a surgical procedure.

The amino acids of the self-assembling or amphiphilic peptides may be selected from d-amino acids, l-amino acids, or combinations thereof. The hydrophobic amino acids may include Ala, Val, Ile, Met, Phe, Tyr, Trp, Ser, Thr and Gly. The hydrophilic amino acids may be basic amino acids, for example, Lys, Arg, His, Orn; acidic amino acids, for example, Glu, Asp; or amino acids which form hydrogen bonds, for example, Asn, Gln. Acidic and basic amino acids may be clustered on a peptide. The carboxyl and amino groups of the terminal residues may be protected or not protected. Membranes or hydrogels may be formed in a homogeneous mixture of self-complementary and self-compatible peptides or in a heterogeneous mixture of peptides which are complementary and structurally compatible to each other. Peptides fitting the above criteria may self-assemble into macroscopic membranes under suitable conditions, described herein.

The self-assembling peptides may be composed of about 6 to about 200 amino acid residues. In certain embodiments, about 7 to about 32 residues may be used in the self-assembling peptides, while in other embodiments self-assembling peptides may have about 7 to about 17 residues. The peptides may have a length of about 5 nm.

The peptides of the present disclosure may include peptides having the repeating sequence of arginine, alanine, aspartic acid and alanine (Arg-Ala-Asp-Ala (RADA) (SEQ ID NO: 1)), and such peptide sequences may be represented by $(RADA)_p$, wherein p=2-50 (SEQ ID NO: 2).

Other peptide sequences may be represented by self-assembling peptides having the repeating sequence of isoleucine, glutamic acid, isoleucine and lysine (Ile-Glu-Ile-Lys (IEIK) (SEQ ID NO: 3)), and such peptide sequences are represented by $(IEIK)_p$, wherein p=2-50 (SEQ ID NO: 4). Other peptide sequences may be represented by self-assembling peptides having the repeating sequence of isoleucine, glutamic acid, isoleucine and lysine (Ile-Glu-Ile-Lys (IEIK) (SEQ ID NO: 3)), and such peptide sequences are represented by $(IEIK)_pI$, wherein p=2-50 (SEQ ID NO: 5).

Other peptide sequences may be represented by self-assembling peptides having the repeating sequence of lysine, leucine, aspartic acid, and leucine (Lys-Leu-Asp-Leu (KLDL) (SEQ ID NO: 6)), and such peptide sequences are represented by $(KLDL)_p$, wherein p=2-50 (SEQ ID NO: 7). Other peptide sequences may be represented by self-assembling peptides having the repeating sequence of lysine, leucine, and aspartic acid (Lys-Leu-Asp (KLD) (SEQ ID NO: 8)), and such peptide sequences are represented by $(KLD)_p$, wherein p=2-50 (SEQ ID NO: 9). As specific examples of self-assembling peptides according to the invention there may be a self-assembling peptide RADA16 having the sequence Arg-Ala-Asp-Ala-Arg-Ala-Asp-Ala-Arg-Ala-Asp-Ala-Arg-Ala-Asp-Ala (RADA)$_4$ (SEQ ID NO: 10), a self-assembling peptide IEIK13 having the sequence Ile-Glu-Ile-Lys-Ile-Glu-Ile-Lys-Ile-Glu-Ile-Lys-Ile (IEIK)$_3$I (SEQ ID NO: 11), a self-assembling peptide IEIK17 having the sequence Ile-Glu-Ile-Lys-Ile-Glu-Ile-Lys-Ile-Glu-Ile-Lys-Ile-Glu-Ile-Lys-Ile (IEIK)$_4$I (SEQ ID NO: 12) or a self-assembling peptide KLDL12 having the sequence Lys-Leu-Asp-Leu-Lys-Leu-Asp-Leu-Lys-Leu-Asp-Leu (KLDL)$_3$ (SEQ ID NO: 13).

Each of the peptide sequences disclosed herein may provide for peptides comprising, consisting essentially of, and consisting of the amino acid sequences recited.

The present disclosure provides materials, methods, and kits for solutions, hydrogels, and scaffolds comprising, consisting essentially of, or consisting of the peptides recited herein.

A 1 weight per volume (w/v) percent aqueous (water) solution and a 2.5 w/v percent of (RADA)$_4$ (SEQ ID NO: 10) is available as the product PuraMatrix™ peptide hydrogel by 3-D Matrix Co., Ltd.

Certain peptides may contain sequences which are similar to the cell attachment ligand RGD (Arginine-Glycine-Aspartic acid). The suitability of these peptides for supporting in vitro cell growth was tested by introducing a variety of cultured primary and transformed cells to homopolymer sheets of Ala-Glu-Ala-Glu-Ala-Lys-Ala-Lys-Ala-Glu-Ala-Glu-Ala-Lys-Ala-Lys (AEAEAKAKAEAEAKAK (EAK16) (SEQ ID NO: 14), RAD 16 (SEQ ID NO: 26), RADA16 (SEQ ID NO: 10), and heteropolymers of RAD16 (SEQ ID NO: 26) and EAK16 (SEQ ID NO: 14). The RAD-based peptides may be of particular interest because the similarity of this sequence to RGD. The RAD sequence is a high affinity ligand present in the extracellular matrix protein tenascin and is recognized by integrin receptors. The EAK 16 peptide (SEQ ID NO: 14) and other peptides disclosed herein were derived from a region of a yeast protein, zuotin.

The self-assembly of the peptides may be attributable to hydrogen bonding and hydrophobic bonding between the peptide molecules by the amino acids composing the peptides.

The self-assembling peptides of the present disclosure may have a nanofiber diameter in a range of about 10 nm to about 20 nm and an average pore size is in a range of about 5 nm to about 200 nm. In certain embodiments, the nanofiber diameter, the pore size, and the nanofiber density may be controlled by at least one of the concentration of peptide solution used and the amount of peptide solution used, such as the volume of peptide solution. As such, at least one of a specific concentration of peptide in solution and a specific amount of peptide solution to provide at least one of a desired nanofiber diameter, pore size, and density to adequately provide for an occlusion may be selected.

As used herein, an amount of a peptide, peptide solution or hydrogel effective to at least partially prevent or reduce a gastrointestinal obstruction, an "effective amount" or a "therapeutically effective amount" refers to an amount of the peptide, peptide solution or hydrogel, which is effective, upon single or multiple administration (application or injection) to a subject, in treating, or in curing, alleviating, relieving or improving a subject with a disorder beyond that expected in the absence of such treatment. This may include a particular concentration or range of concentrations of peptide in the peptide solution or hydrogel and additionally, or in the alternative, a particular volume or range of volumes of the peptide solution or hydrogel. The method of facilitating may comprise providing instructions to prepare at least one of the effective amount and the effective concentration.

The dosage, for example, volume or concentration, administered (for example, applied or injected) may vary depending upon the form of the peptide (for example, in a peptide solution, hydrogel, or in a dried form, such as a lyophilized form) and the route of administration utilized. The exact formulation, route of administration, volume, and concentration can be chosen in view of the subject's condition and in view of the particular target area or location that the peptide solution, hydrogel, or other form of peptide will be administered. Lower or higher doses than those recited herein may be used or required. Specific dosage and treatment regimens for any particular subject may depend upon a variety of factors, which may include the specific peptide or peptides employed, the dimension of the area that is being treated, the desired thickness of the resulting hydrogel that may be positioned in the desired target area, and the length of time of treatment. Other factors that may affect the specific dosage and treatment regimens include age, body weight, general health status, sex, time of administration, rate of degradation, the severity and course of the disease, condition or symptoms, and the judgment of the treating physician. In certain embodiments, the peptide solution may be administered in a single dose. In other embodiments, the peptide solution may be administered in more than one dose, or multiple doses. The peptide solution may be administered in at least two doses.

An effective amount and an effective concentration of the peptide solution may be selected to at least partially prevent or reduce a gastrointestinal obstruction. In some embodiments, at least one of the effective amount and the effective concentration may be based in part on a dimension or diameter of the target area. In other embodiments, at least one of the effective amount and the effective concentration is based in part on the flow rate of one or more fluids at or near the target area. In still other embodiments, at least one of the effective amount and the effective concentration may be based in part on a dimension or diameter of a material being removed from the gastrointestinal tract, such as tissue, or a tumor.

In yet other embodiments, at least one of the effective amount and the effective concentration may be based in part on at least one of a dimension or diameter of the target area, the flow rate of one or more fluids at or near the target area, and on a dimension or diameter of a material being removed from the gastrointestinal tract, such as tissue, or a tumor.

The effective amount may be, as described herein, an amount that may provide for an at least partial prevention or reduction in a gastrointestinal obstruction. Various properties of the gastrointestinal tract may contribute to the selection or determination of the effective amount including at least one of the dimension or diameter of the target area, the flow rate of one or more fluids at or near the target area, the pH at or near the target area, and the concentration of various salts at or near the target area. Additional properties that may determine the effective amount include various properties list above, at various locations along a pathway in which the peptide solution is delivered. For example, if the target area is located in the stomach, one or more properties of the stomach and/or one or more properties of the pathway to the stomach, for example, the esophagus, may at least partially influence or effect the selection or determination of the effective amount.

The effective amount may include volumes of from about 0.1 milliliters (mL) to about 100 mL of a peptide solution. The effective amount may include volumes of from about 0.1 mL to about 10 mL of a peptide solution. In certain embodiments, the effective amount may be about 0.5 mL. In other embodiments, the effective amount may be about 1.0 mL. In yet other embodiments, the effective amount may be about 1.5 mL. In still yet other embodiments, the effective amount may be about 2.0 mL. In some other embodiments, the effective amount may be about 3.0 mL. In certain embodiments, the effective amount may be approximately 0.1 mL to about 5 mL per 1 cm$^2$ of target area. In certain embodiments, the effective amount may be approximately 1 mL per 1 cm$^2$ of target area. This effective amount may be used related to a concentration, such as a 2.5 weight per volume percent of a peptide solution of the present disclosure.

In some embodiments, a more effective prevention or reduction in gastrointestinal obstruction may be achieved with a greater volume of peptide solution administered or a higher concentration of peptide in solution to be administered. This may allow a longer or thicker hydrogel to form within the target area, allowing a more secure position of the hydrogel in the target area. It is possible that if a high enough volume is not selected, the hydrogel may not be effective in preventing or reducing a gastrointestinal obstruction in the target area for the desired period of time.

The effective concentration may be, as described herein, an amount that may provide for a desired prevention or reduction in gastrointestinal obstruction. Various properties of the gastrointestinal tract may contribute to the selection or determination of the effective concentration including at least one of a dimension or diameter of the target area, the flow rate of one or more fluids at or near the target area, and on a dimension or diameter of a material being removed from the gastrointestinal tract, such as tissue, or a tumor.

The effective concentration may include peptide concentrations in the solution in a range of about 0.1 weight per volume (w/v) percent to about 10 w/v percent. The effective concentration may include peptide concentrations in the solution in a range of about 0.1 w/v percent to about 3.5 w/v percent. In certain embodiments, the effective concentration may be about 1 w/v percent. In other embodiments, the effective concentration may be about 2.5 w/v percent. In yet other embodiments, the effective concentration may be about 3.0 w/v percent.

In certain embodiments, a peptide solution having a higher concentration of peptide may provide for a more effective hydrogel that has the ability to stay in place and provide effective prevention or reduction in gastrointestinal obstruction. For purposes of delivering the peptide solution, higher concentrations of peptide solutions may become too viscous to allow for effective and selective administration of the solution. It is possible that if a high enough concentration is not selected, the hydrogel may not be effective in maintaining a prevention or reduction in gastrointestinal obstruction in the target area for the desired period of time.

The effective concentration may be selected to provide for a solution that may be administered by injection or other means using a particular diameter or gauge catheter or needle.

Methods of the disclosure contemplate single as well as multiple administrations of a therapeutically effective amount of the peptides, compositions, peptide solutions, membranes, filaments, and hydrogels as described herein. Peptides as described herein may be administered at regular intervals, depending on the nature, severity and extent of the subject's condition. In some embodiments, a peptide, composition, peptide solution, membrane, filament, or hydrogel may be administered in a single administration. In some embodiments, a peptide, composition, peptide solution, or hydrogel described herein is administered in multiple administrations. In some embodiments, a therapeutically effective amount of a peptide, composition, peptide solution, membrane, filament, or hydrogel may be administered periodically at regular intervals. The regular intervals selected may be based on any one or more of the initial peptide concentration of the solution administered, the amount administered, and the degradation rate of the hydrogel formed. For example, after an initial administration, a follow-on administration may occur after, for example, one week, two weeks, four weeks, six weeks, or eight weeks. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging the target area and the area surrounding the target area and ascertaining the needs based on the condition of the subject. The pre-determined intervals may be the same for each follow-on administration, or they may be different. In some embodiments, a peptide, peptide solution, or hydrogel may be administered chronically at pre-determined intervals to maintain at least a partial prevention or reduction in gastrointestinal obstruction in a subject over the life of the subject. The pre-determined intervals may be the same for each follow-on administration, or they may be different. This may be dependent on whether the hydrogel formed from the previous administration is partially or totally disrupted or degraded. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging the target area and the area surrounding the target area and ascertaining the needs based on the condition of the subject.

The self-assembling peptides of the present disclosure, such as RADA16 (SEQ ID NO: 10), may be peptide sequences that lack a distinct physiologically or biologically active motif or sequence, and therefore may not impair intrinsic cell function. Physiologically active motifs may control numerous intracellular phenomena such as transcription, and the presence of physiologically active motifs may lead to phosphorylation of intracytoplasmic or cell surface proteins by enzymes that recognize the motifs. When a physiologically active motif is present in a peptide tissue occluding agent, transcription of proteins with various functions may be activated or suppressed. The self-assembling peptides, of the present disclosure may lack such physiologically active motifs and therefore do not carry this risk.

A sugar may be added to the self-assembling peptide solution to improve the osmotic pressure of the solution from hypotonicity to isotonicity without reducing the tissue occluding effect, thereby allowing the biological safety to be increased. In certain examples, the sugar may be sucrose or glucose.

The optimal lengths for membrane formation may vary with the amino acid composition. A stabilization factor contemplated by the peptides of the present disclosure is that complementary peptides maintain a constant distance between the peptide backbones. Peptides which can maintain a constant distance upon pairing are referred to herein as structurally compatible. The interpeptide distance can be calculated for each ionized or hydrogen bonding pair by taking the sum of the number of unbranched atoms on the side-chains of each amino acid in the pair. For example, lysine has 5 and glutamic acid has 4 unbranched atoms on its side-chains, respectively. Other examples of peptides that may form membranes, hydrogels or scaffolds in homogeneous or heterogeneous mixtures are listed in Table 1.

TABLE 1

Potential hydrogel-forming peptides

| Name | Sequence (N→C) |
|---|---|
| KAKA16 | KAKAKAKAKAKAKAKA (SEQ ID NO: 15) |
| KAKA5 | KAKAK (SEQ ID NO: 16) |
| KAE16 | AKAKAEAEAKAKAEAE (SEQ ID NO: 17) |
| AKE16 | AKAEAKAEAKAEAKAE (SEQ ID NO: 18) |
| EKA16 | EAKAEAKAEAKAEAKA (SEQ ID NO: 19) |
| EAK8 | AEAEAKAK (SEQ ID NO: 20) |
| EAK12 | AEAKAEAEAKAK (SEQ ID NO: 21) |
| KEA16 | KAEAKAEAKAEAKAEA (SEQ ID NO: 22) |
| AEK16 | AEAKAEAKAEAKAEAK (SEQ ID NO: 23) |
| ARD8 | ARARADAD (SEQ ID NO: 24) |
| DAR16 | ADADARARADADARAR (SEQ ID NO: 25) |
| RAD16 | ARADARADARADARAD (SEQ ID NO: 26) |
| DRA16 | DARADARADARADARA (SEQ ID NO: 27) |
| RADA16 | RADARADARADARADA (SEQ ID NO: 10) |
| ADR16 | ADARADARADARADAR (SEQ ID NO: 28) |
| ARA16 | ARARADADARARADAD (SEQ ID NO: 29) |
| ARDAKE16 | ARADAKAEARADAKAE (SEQ ID NO: 30) |
| AKEW16 | AKAEARADAKAEARAD (SEQ ID NO: 31) |
| ARKADE16 | ARAKADAEARAKADAE (SEQ ID NO: 32) |
| AKRAED16 | AKARAEADAKARADAE (SEQ ID NO: 33) |
| AQ16 | AQAQAQAQAQAQAQAQ (SEQ ID NO: 34) |

TABLE 1-continued

Potential hydrogel-forming peptides

| Name | Sequence (N→C) |
|---|---|
| VQ16 | VQVQVQVQVQVQVQVQ (SEQ ID NO: 35) |
| YQ16 | YQYQYQYQYQYQYQYQ (SEQ ID NO: 36) |
| HQ16 | HQHQHQHQHQHQHQHQ (SEQ ID NO: 37) |
| AN16 | ANANANANANANANAN (SEQ ID NO: 38) |
| VN16 | VNVNVNVNVNVNVNVN (SEQ ID NO: 39) |
| YN16 | YNYNYNYNYNYNYNYN (SEQ ID NO: 40) |
| HN16 | HNHNHNHNHNHNHNHN (SEQ ID NO: 41) |
| ANQ16 | ANAQANAQANAQANAQ (SEQ ID NO: 42) |
| AQN16 | AQANAQANAQANAQAN (SEQ ID NO: 43) |
| VNQ16 | VNVQVNVQVNVQVNVQ (SEQ ID NO: 44) |
| VQK16 | VQVNVQVNVQVNVQVN (SEQ ID NO: 45) |
| YNQ16 | YNYQYNYQYNYQYNYQ (SEQ ID NO: 46) |
| YQN16 | YQYNYQYNYQYNYQYN (SEQ ID NO: 47) |
| HNQ16 | HNHQHNHQHNHQHNHQ (SEQ ID NO: 48) |
| HQN16 | HQHNHQHNHQHNHQHN (SEQ ID NO: 49) |
| AKQD18 | AKAQADAKAQADAKAQAD (SEQ ID NO: 50) |
| VKQ18 | VKVQVDVKVQVDVKVQVD (SEQ ID NO: 51) |
| YKQ18 | YKYQYDYKYQYDYKYQYD (SEQ ID NO: 52) |
| HKQ18 | HKHQHDHKHQHDHKHQHD (SEQ ID NO: 53) |
| RADA | RADA (SEQ ID NO: 1) |
| IEIK | IEIK (SEQ ID NO: 3) |
| ATAT | ATAT (SEQ ID NO: 54) |
| TVTV | TVTV (SEQ ID NO: 55) |
| ASAS | ASAS (SEQ ID NO: 56) |
| SSSS | SSSS (SEQ ID NO: 57) |

TABLE 1-continued

Potential hydrogel-forming peptides

| Name | Sequence (N→C) |
|---|---|
| | VVVTTTT (SEQ ID NO: 58) |
| | RAD (SEQ ID NO: 59) |
| | KLD (SEQ ID NO: 8) |
| | AAAAAAK (SEQ ID NO: 60) |
| | AAAAAAD (SEQ ID NO: 61) |
| | ATATATAT (SEQ ID NO: 62) |
| | TVTVTVTV (SEQ ID NO: 63) |
| | ASASASAS (SEQ ID NO: 64) |
| | SSSSSSS (SEQ ID NO: 65) |

The criteria of amphiphilic sequence, length, complementarity and structural compatibility apply to heterogeneous mixtures of peptides. For example, two different peptides may be used to form the membranes: peptide A, Val-Arg-Val-Arg-Val-Asp-Val-Asp-Val-Arg-Val-Arg-Val-Asp-Val-Asp (VRVRVDVDVRVRVDVD) (SEQ ID NO: 66), has Arg and Asp as the hydrophilic residues and peptide B, Ala-Asp-Ala-Asp-Ala-Lys-Ala-Lys-Ala-Asp-Ala-Asp-Ala-Lys-Ala-Lys (ADADAKAKADADAKAK) (SEQ ID NO: 67), has Lys and Asp. Peptides A and B are complementary; the Arg on A can form an ionized pair with the Asp on B and the Asp on A can form an ionized pair with the Lys on B. Thus, in a heterogeneous mixture of peptides A and B, membranes would likely form, but they would be homogeneously composed of either peptide A or B.

Membranes and hydrogels can also be formed of heterogeneous mixtures of peptides, each of which alone would not form membranes, if they are complementary and structurally compatible to each other. For example, mixtures of (Lys-Ala-Lys-Ala)$_4$ (KAKA)$_4$ (SEQ ID NO: 15) and (Glu-Ala-Glu-Ala)$_4$ (EAEA)$_4$ (SEQ ID NO: 68) or of (Lys-Ala-Lys-Ala)$_4$ (KAKA)$_4$ (SEQ ID NO: 15) and (Ala-Asp-Ala-Asp)$_4$ (ADAD)$_4$ (SEQ ID NO: 69) would be expected to form membranes, but not any of these peptides alone due to lack of complementarity.

Peptides, which are not perfectly complementary or structurally compatible, can be thought of as containing mismatches analogous to mismatched base pairs in the hybridization of nucleic acids. Peptides containing mismatches can form membranes if the disruptive force of the mismatched pair is dominated by the overall stability of the interpeptide interaction. Functionally, such peptides can also be considered as complementary or structurally compatible. For example, a mismatched amino acid pair may be tolerated if it is surrounded by several perfectly matched pairs on each side.

The peptides can be chemically synthesized or they can be purified from natural and recombinant sources. Using chemically synthesized peptides may allow the peptide solutions to be deficient in unidentified components such as unidentified components derived from the extracellular matrix of another animal. This property therefore may eliminate concerns of infection, including risk of viral infection compared to conventional tissue-derived biomaterials. This may eliminate concerns of infection including infections such as bovine spongiform encephalopathy (BSE), making the peptide highly safe for medical use.

The initial concentration of the peptide may be a factor in the size and thickness of the membrane, hydrogel, or scaffold formed. In general, the higher the peptide concentration, the higher the extent of membrane or hydrogel formation. Hydrogels, or scaffolds formed at higher initial peptide concentrations (about 10 mg/ml) (about 1.0 w/v percent) may be thicker and thus, likely to be stronger.

Formation of the, membranes, hydrogels, or scaffolds may be very fast, on the order of a few minutes. The formation of the membranes or hydrogels may be irreversible. In certain embodiments, the formation may be reversible, and in other embodiments, the formation may be irreversible. The hydrogel may form instantaneously upon administration to a target area. The formation of the hydrogel may occur within about one to two minutes of administration. In other examples, the formation of the hydrogel may occur within about three to four minutes of administration. In certain embodiments the time it takes to form the hydrogel may be based at least in part on one or more of the concentration of the peptide solution, the volume of peptide solution applied, and the conditions at the area of application or injection (for example, the concentration of monovalent metal cations at the area of application, the pH of the area, and the presence of one or more fluids at or near the area). The process may be unaffected by pH of less than or equal to 12, and by temperature. The membranes or hydrogels may form at temperatures in the range of about 1 to 99 degrees Celsius.

The hydrogels may remain in position at the target area for a period of time sufficient to provide a desired effect using the methods and kits of the present disclosure. The desired effect may be to at least partially prevent or reduce a gastrointestinal obstruction.

The desired effect using the methods and kits of the present disclosure may be to treat areas or to assist in healing of areas in which a surgical procedure in the gastrointestinal tract was performed. For example, the desired effect using the methods and kits of the present disclosure may be to treat areas or to assist in healing of areas in which resection of lesion sites such as polyps and cancerous tumors in the gastrointestinal tract. Surgical procedures may include endoscopic mucosal resection (EMR) or endoscopic submucosal dissection (ESD).

The period of time that the membranes or hydrogels may remain at the desired area may be for one or more days, up to one or more weeks. In other examples, it may remain at the desired area for up to 30 days, or more. It may remain at the desired area indefinitely. In other examples, it may remain at the desired area for a longer period of time, until it is naturally degraded or intentionally removed. If the hydrogel naturally degrades over a period of time, subsequent application or injection of the hydrogel to the same or different location may be performed.

In certain embodiments, the self-assembling peptide may be prepared with one or more components that may provide for enhanced effectiveness of the self-assembling peptide or may provide another action, treatment, therapy, or otherwise interact with one or more components of the subject. For example, additional peptides comprising one or more biologically or physiologically active amino acid sequences or motifs may be included as one of the components along with the self-assembling peptide. Other components may include biologically active compounds such as a drug or other treatment that may provide some benefit to the subject. For example, a cancer treating drug or anticancer drug may be administered with the self-assembling peptide, or may be administered separately.

The peptide, peptide solution, or hydrogel may comprise small molecular drugs to treat the subject or to prevent hemolysis, inflammation, and infection. The small molecular drugs may be selected from the group consisting of glucose, saccharose, purified saccharose, lactose, maltose, trehalose, destran, iodine, lysozyme chloride, dimethylisoprpylazulene, tretinoin tocoferil, povidone iodine, alprostadil alfadex, anise alcohol, isoamyl salicylate, $\alpha,\alpha$-dimethylphenylethyl alcohol, bacdanol, helional, sulfazin silver, bucladesine sodium, alprostadil alfadex, gentamycin sulfate, tetracycline hydrochloride, sodium fusidate, mupirocin calcium hydrate and isoamyl benzoate. Other small molecular drugs may be contemplated. Protein-based drugs may be included as a component to be administered, and may include erythropoietin, tissue type plasminogen activator, synthetic hemoglobin and insulin.

A component may be included to protect the peptide solution against rapid or immediate formation into a hydrogel. This may include an encapsulated delivery system that may degrade over time to allow a controlled time release of the peptide solution into the target area to form the hydrogel over a desired, predetermined period of time. Biodegradable, biocompatible polymers may be used, such as ethylene vinyl acetate, polyanhydrides, polyglycolic acid, collagen, polyorthoesters, and polylactic acid.

Any of the components described herein may be included in the peptide solution or may be administered separate from the peptide solution. Additionally, any of the methods and methods of facilitating provided herein may be performed by one or more parties.

A peptide, peptide solution, or hydrogel of the disclosure may be provided in a kit. Instructions for administering the solution to a target area of the gastrointestinal tract of a subject may also be provided in the kit. The peptide solution may comprise a self-assembling peptide comprising between about 7 amino acids and about 32 in an effective amount and in an effective concentration to form a hydrogel to at least partially prevent or reduce a gastrointestinal obstruction. The instructions for administering the solution may comprise methods for administering the peptide, peptide solution, or hydrogel provided herein, for example, by a route of administration described herein, at a dose, volume or concentration, or administration schedule. The peptide may be amphiphilic and at least a portion of the peptide may alternate between a hydrophobic amino acid and a hydrophilic amino acid.

The kit may also comprise informational material. The informational material may be descriptive, instructional, marketing or other material that relates to the methods described herein. In one embodiment, the informational material may include information about production of the peptide, peptide solution, or hydrogel disclosed herein, physical properties of the peptide, composition, peptide solution or hydrogel, concentration, volume, size, dimensions, date of expiration, and batch or production site.

The kit may also optionally include a device or materials to allow for administration of the peptide or peptide solution to the desired area. For example, a syringe, pipette, tube, catheter, syringe catheter, or other needle-based device may be included in the kit. Additionally, or alternatively, the kit may include a guidewire, endoscope, or other accompanying equipment to provide selective administration of the peptide solution to the target area.

The kit may comprise in addition to or in the alternative, other components or ingredients, such as components that may aid in positioning of the peptide solution, hydrogel or scaffold. Instructions may be provided in the kit to combine a sufficient quantity or volume of the peptide solution with a sucrose solution, that may or may not be provided with the kit. Instructions may be provided for diluting the peptide solution to administer an effective concentration of the solution to the target area of the gastrointestinal tract. The instruction may describe diluting the peptide solution with a diluant or solvent. The diluant or solvent may be water. Instructions may further be provided for determining at least one of the effective concentration of the solution and the effective amount of the solution to the target area. This may be based on various parameters discussed herein, and may include the diameter of the lesion or wound at the target area.

Other components or ingredients may be included in the kit, in the same or different compositions or containers than the peptide, peptide solutions, or hydrogel. The one or more components that may include components that may provide for enhanced effectiveness of the self-assembling peptide or may provide another action, treatment, therapy, or otherwise interact with one or more components of the subject. For example, additional peptides comprising one or more biologically or physiologically active sequences or motifs may be included as one of the components along with the self-assembling peptide. Other components may include biologically active compounds such as a drug or other treatment that may provide some benefit to the subject. For example, a cancer treating drug or anticancer drug may be administered with the self-assembling peptide, or may be administered separately. The peptide, peptide solution, or hydrogel may comprise small molecular drugs to treat the subject or to prevent hemolysis, inflammation, and infection, as disclosed herein. A sugar solution such as a sucrose solution may be provided with the kit. The sucrose solution may be a 20% sucrose solution.

Other components which are disclosed herein may also be included in the kit.

In some embodiments, a component of the kit is stored in a sealed vial, for example, with a rubber or silicone closure (for example, a polybutadiene or polyisoprene closure). In some embodiments, a component of the kit is stored under inert conditions (for example, under nitrogen or another inert gas such as argon). In some embodiments, a component of the kit is stored under anhydrous conditions (for example, with a desiccant). In some embodiments, a component of the kit is stored in a light blocking container such as an amber vial.

As part of the kit or separate from a kit, syringes or pipettes may be pre-filled with a peptide, peptide solution, or hydrogel as disclosed herein. Methods to instruct a user to supply a self-assembling peptide solution to a syringe or pipette, with or without the use of other devices, and administering it to the target area through the syringe or pipette, with or without the use of other devices, is provided. Other devices may include, for example, a catheter with or without a guidewire.

In some embodiments of the disclosure, the self-assembling peptides may be used as a coating on a device or an instrument such as a stent or catheter, to suppress body fluid leakage. The self-assembling peptides may also be incorporated or secured to a support, such as gauze or a bandage, or a lining, that may provide a therapeutic effect to a subject, or that may be applied within a target area. The self-assembling peptides may also be soaked into a sponge for use.

The membranes may also be useful for culturing cell monolayers. Cells prefer to adhere to non-uniform, charged surfaces. The charged residues and conformation of the proteinaceous membranes promote cell adhesion and migration. The addition of growth factors, such as fibroblast growth factor, to the peptide membrane may further improve attachment, cell growth and neurite outgrowth.

The function and advantage of these and other embodiments of the methods and kits disclosed herein will be more fully understood from the example below. The following example is intended to illustrate the benefits of the disclosed treatment approach, but do not exemplify the full scope thereof.

EXAMPLES

Example 1

Figure 1B:
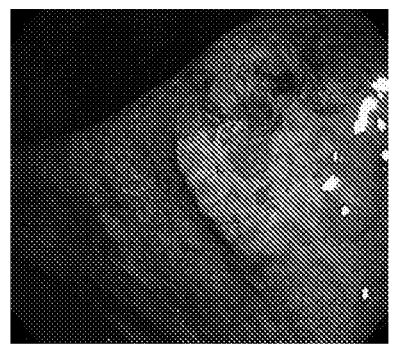
FIG. 1B is an image of an ulcer prior to ESD, in accordance with some embodiments.

Testing was performed in human subjects in order to determine the ability of disclosed peptides to prevent gastrointestinal obstruction. Subjects who underwent esophageal, gastric, and colorectal endoscopic submucosal dissection (ESD) by nine endoscopists participated in the testing. Subjects receiving antithrombotic therapy were included in the study, but such medications were no longer being administered prior to the procedures. Cases with perforation and coagulopathy (international normalized ratio (INR)>3) despite anticoaculation management after heparin bridge therapy (HBT) were excluded. FIGS. 1A and 1B shows an ulcer prior to ESD.

Figure 1C:
FIG. 1C is an image showing an area soon after ESD, in accordance with some embodiments.

After the ESD procedure, a self-assembling peptide was administered to a target area in the subject. FIG. 1C shows an area soon after ESD. For every 1 cm$^2$ of tumor, 1 mL of self-assembling peptide RADA16, in the form of PuraMatrix™ peptide hydrogel by 3-D Matrix, LTD. (2.5 w/v percent) was applied to the ESD-induced ulcer using a catheter immediately after the procedure. A single dose proton pump inhibitor was administered in gastric ESD cases for 8 weeks beginning the morning of the procedure. Gastric ulcer stages were evaluated by endoscopy as active, healing or scarring at 1, 4, and 8 weeks after ESDs, and application of the self-assembling peptide. The primary endpoint was the rate of post-ESD bleeding. The secondary endpoints include the transitional rate to healing and scarring stages of gastric ESD-induced ulcers.

Of the 117 subjects recruited, 114 patients with 124 lesions (esophagus 18; stomach 42; colorectum 64) were enrolled for outcome analysis and 3 subjects were excluded due to perforations and 1 with coagulopathy.

Figure 1D:
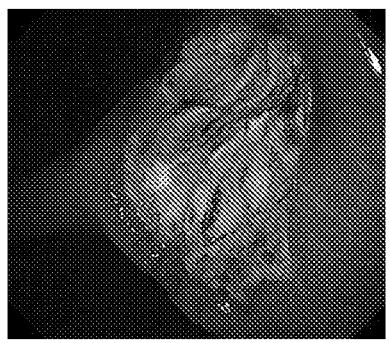
FIG. 1D is an image showing the area 1 week after ESD and peptide solution application, in accordance with some embodiments.
Figure 1E:
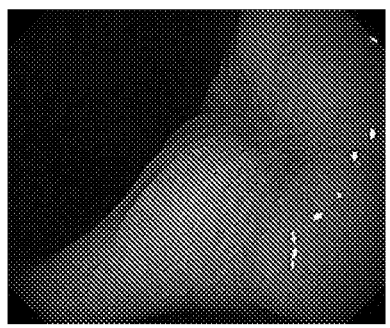
FIG. 1E is an image showing the area 4 weeks after ESD and peptide application, in accordance with some embodiments.
Figure 1F:
FIG. 1F is an image showing the area 8 weeks after ESD and peptide application, in accordance with some embodiments.

Of the 114 subjects, 22 (19%) were previously on antithrombotic therapy including 6 (5%) requiring HBTs. The mean size of resected specimen was 40±16 mm (esophagus 41±20 mm; stomach 36±12 mm; colorectum 43±16 mm). The rate of post-ESD bleeding was 1.6% (2/124) (esophagus 0%; stomach 2.4% (1/43' 95% confidence interval, 0.04% to 12.3%); colorectum 1.6% (1/64' 95%0, 0.02% to 1.6%). All post-ESD bleedings was successfully managed endoscopically without needed blood transfusion. Transitional rate to healing stage at 1 week was 98%. FIG. 1D shows the area 1 week after ESD and peptide application. Follow up endoscopies demonstrated scarring stage in 21% and 97% at 4 and 8 weeks respectively. FIG. 1E shows the area 4 weeks after ESD and peptide application. FIG. 1F shows the area 8 weeks after ESD and peptide application.

This testing demonstrated the usefulness and effectiveness of applying a self-assembling peptide to the site of a post-ESD lesion. There were no adverse effects related with the use of the self-assembling peptide. The self-assembling peptide helped reduce post-ESD bleeding rate. The self-assembling peptide also promoted ulcer healing. The self-assembling peptides of the present disclosure provided enhanced treatment and recovery of the subjects tested, indicating the effectiveness of the use of this peptide for treating ESD-induced ulcers.

Example 2

Figure 2A:
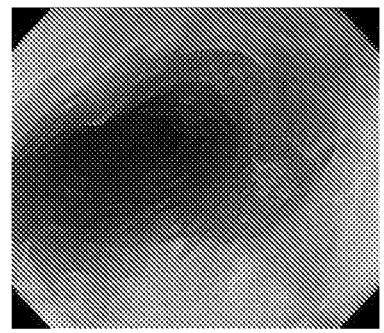
FIG. 2A is an image showing an early-stage esophageal cancer with a ¾ circumferential spread, in accordance with some embodiments.
Figure 2B:
FIG. 2B is an image showing an artificial ulcer with a ⅘ circumferential spread after the lesion is resected using ESD, in accordance with some embodiments.

Verification of PuraMatrix™ Peptide Hydrogel's Effectiveness as a Stenosis Preventive after an Endoscopic Resection for Large-Scale Early-Stage Gastrointestinal Cancer and Precancerous Lesions in Humans Testing was performed on a subject having an ulcer (lesion) after an endoscopic resection of esophageal cancer. As shown in FIG. 2A, an early-stage esophageal cancer with a ¾ circumferential spread is shown, in that the cancer site covers ¾ of a circular area. Endoscopic submucosal dissection was performed, which created an ulcer. FIG. 2B shows an artificial ulcer with a ⅘ circumferential spread, in that the resected lesion covers ⅘ of a circular area, after the lesion is resected using ESD. A ⅘ circumferential spread may cause stenosis in the absence of applying a peptide solution to form a hydrogel.

Figure 2C:
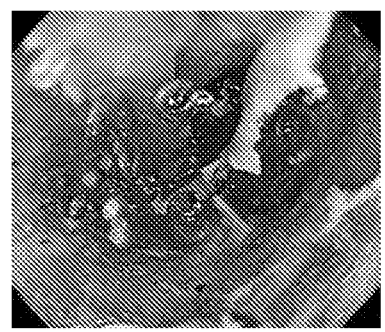
FIG. 2C is an image showing a coating of a peptide solution, in accordance with some embodiments.

After confirming that there was no hemorrhaging in the artificial ulcer surface after an endoscopic resection, a catheter was passed through an endoscope, and a peptide solution such as PuraMatrix™ peptide hydrogel by 3-D Matrix, LTD. (2.5%, suitable dose (1 mL per 1 cm$^2$)) in a syringe was coated evenly over the ulcer surface. FIG. 2C shows a coating of the peptide solution.

Figure 2D:
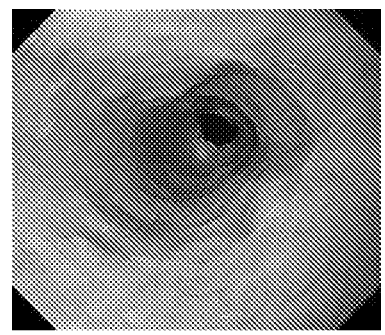
FIG. 2D is an image showing a treated area 4 weeks after surgery, in accordance with some embodiments.
Figure 2E:
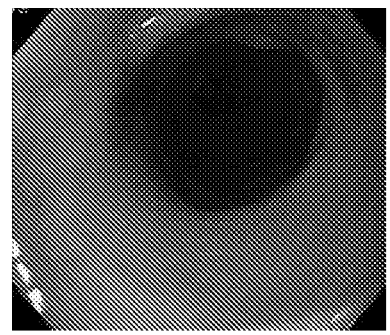
FIG. 2E is an image of the treated area 8 weeks after surgery, in accordance with some embodiments.

On the first week after surgery, an endoscope is used to review the area. At this time, as with the initial round, the peptide solution is coated evenly over the ulcer surface. For past cases, an endoscope was used to perform a third and fourth review of the area, in the fourth and eighth weeks, respectively, after surgery that induced stenosis, to judge the effectiveness of the peptide solution coating. FIG. 2D shows the treated area 4 weeks after surgery. The ulcer shows scarring, and the endoscope passage is possible in the stenosis direction. FIG. 2E shows the treated area 8 weeks after surgery. The endoscope passage is possible in stenosis direction.

The effectiveness of the peptide solution as a stenosis preventive was demonstrated. In addition, no delayed hemorrhaging or perforations were seen as side effects of the endoscopic resection.

This Example demonstrates the ability of the peptide solution to form a hydrogel on an ulcer surface to promote healing of the area and reduce stenosis.

The invention claimed is:

1. A method of preventing stenosis in one or more of the mouth, throat, and esophagus in a subject, comprising:
   introducing a catheter into the mouth, throat, or esophagus;
   positioning an end of the catheter in a target area of the mouth, throat, or esophagus in which a prevention of stenosis is desired;
   administering through the catheter a solution comprising a self-assembling peptide in an effective amount and in an effective concentration to form a hydrogel under conditions of the mouth, throat, or esophagus to allow prevention of stenosis; and
   removing the catheter from the mouth, throat, or esophagus;
   wherein the self-assembling peptide is between about 7 amino acids and about 32 amino acids in length.

2. The method of claim 1, further comprising visualizing a region comprising at least a portion of the mouth, throat, or esophagus.

3. The method of claim 2, wherein visualizing the region comprises visualizing the region during at least one of:
   identifying the target area of the mouth, throat, or esophagus;
   introducing the catheter;
   positioning the end of the catheter in the target area;
   administering the solution;
   removing the catheter; and
   monitoring the mouth, throat, or esophagus after removing the catheter.

4. The method of claim 3, wherein visualizing the region provides for selective administration of the solution to the target area.

5. The method of claim 3, further comprising visualizing the region in a time period about one week subsequent the administration.

6. The method of claim 5, further comprising visualizing the region in a time period about four weeks subsequent the administration.

7. The method of claim 6, further comprising visualizing the region in a time period about eight weeks subsequent the administration.

8. The method of claim 1, wherein at least one of the effective amount and the effective concentration is based in part on a dimension of the target area of the mouth, throat, or esophagus.

9. The method of claim 1, wherein the effective amount is approximately 1 mL per 1 $cm^2$ of target area.

10. The method of claim 1, wherein the concentration effective to allow prevention of stenosis comprises a concentration in a range of about 0.1 weight per volume (w/v) percent to about 3 w/v percent peptide.

11. The method of claim 1, wherein the amount effective to allow prevention of stenosis comprises a volume in a range of about 0.1 mL to about 5 mL.

12. The method of claim 1, further comprising monitoring the target area to determine an effectiveness of the administration of the solution.

13. The method of claim 1, used after a surgical procedure.

14. The method of claim 13, wherein the surgical procedure is one of endoscopic mucosal resection and endoscopic submucosal dissection.

15. The method of claim 1, wherein the solution is substantially free of cells.

16. The method of claim 1, wherein the solution is substantially free of drugs.

17. The method of claim 1, wherein the self-assembling peptide is amphiphilic and consists essentially of between 12 amino acids and 32 amino acids that alternate between a hydrophobic amino acid and a hydrophilic amino acid.

18. The method of claim 17, wherein the self-assembling peptide is amphiphilic and consists of between 12 amino acids and 32 amino acids that alternate between a hydrophobic amino acid and a hydrophilic amino acid.

19. The method of claim 1, wherein the subject is a mammal.

20. The method of claim 19, wherein the subject is human.

21. The method of claim 1, wherein administering the solution comprises administering the solution in a single dose.

22. The method of claim 1, wherein administering the solution comprises administering the solution in at least two doses.

23. The method of claim 1, further comprising evaluating the subject to determine a need for preventing stenosis and preparing the solution.

24. The method of claim 1, further comprising introducing an endoscope into the mouth, throat, or esophagus prior to introducing the catheter.

25. The method of claim 1, wherein the solution further comprises at least one biologically active agent.

26. The method of claim 1, wherein the self-assembling peptide is one of (RADA)$_p$, wherein p=2-8 (SEQ ID NO: 2) and (IEIK)$_p$1, wherein p=2-8 (SEQ ID NO: 5).

27. The method of claim 1, wherein the self-assembling peptide comprises one of (RADA)$_4$ (SEQ ID NO: 10) and (IEIK)$_3$1 (SEQ ID NO: 11).

28. The method of claim 27, wherein the self-assembling peptide consists essentially of one of (RADA)$_4$ (SEQ ID NO: 10) and (IEIK)$_3$1 (SEQ ID NO: 11).

29. A method of facilitating prevention of stenosis in one or more of the mouth, throat, and esophagus of a subject, comprising:
   providing a peptide solution comprising a self-assembling peptide in an effective amount and in an effective concentration to form a hydrogel under physiological conditions to allow prevention of the stenosis;
   providing a sucrose solution in a sufficient quantity or volume to create an isotonic osmotic pressure when added to the peptide solution;
   preparing a combined solution comprising the peptide solution and the sucrose solution; and
   administering the combined solution to a target area of the mouth, throat, or esophagus through introduction of the combined solution through a catheter positioned in the mouth, throat, or esophagus;
   wherein the self-assembling peptide is between about 7 amino acids and 32 amino acids in length.

30. The method of claim 29, further comprising visualizing the region comprising at least a portion of the mouth, throat, or esophagus during at least one of:
   identifying the target area of the gastrointestinal tract;
   introducing a catheter; positioning an end of the catheter in the target area;
   administering the combined solution;
   removing the catheter from the mouth, throat, or esophagus; and
   monitoring the mouth, throat, or esophagus after removing the catheter.

31. The method of claim 30, wherein visualizing the region comprises imaging using an endoscope.

32. The method of claim 30, further comprising visualizing the region in a time period about one week subsequent the administration.

33. The method of claim 32, further comprising visualizing the region in a time period about four weeks subsequent the administration.

34. The method of claim 31, further comprising visualizing the region in a time period about eight weeks subsequent the administration.

35. The method of claim 29, further comprising preparing at least one of the effective amount and the effective concentration based in part on a dimension of the target area of the mouth, throat, or esophagus.

36. The method of claim 29, wherein the effective amount is approximately 1 mL per 1 cm$^2$ of target area.

37. The method of claim 29, wherein the concentration effective to allow prevention of the stenosis comprises a concentration in a range of about 0.1 weight per volume percent to about 3 weight per volume percent peptide.

38. The method of claim 29, wherein the amount effective to allow prevention of the stenosis comprises a volume in a range of about 0.1 mL to about 5 mL.

39. The method of claim 29, further comprising monitoring the area surrounding the target area.

40. The method of claim 29, used after a surgical procedure.

41. The method of claim 40, wherein the surgical procedure is one of endoscopic mucosal resection and endoscopic submucosal dissection.

42. The method of claim 29, wherein the solution is substantially free of cells.

43. The method of claim 29, wherein the solution is substantially free of drugs.

44. The method of claim 29, wherein the self-assembling peptide is between 7 amino acids and 32 amino acids in length.

45. The method of claim 44, wherein the self-assembling peptide is amphiphilic.

46. The method of claim 29, wherein the subject is a mammal.

47. The method of claim 46, wherein the subject is human.

48. The method of claim 29, wherein administering the combined solution comprises administering the combined solution in a single dose.

49. The method of claim 29, wherein administering the combined solution comprises administering the combined solution in at least two doses.

50. The method of claim 29, further comprising evaluating the subject to determine a need for preventing stenosis.

51. The method of claim 29, further comprising introducing an endoscope into the mouth, throat, or esophagus prior to introducing the catheter.

52. The method of claim 29, wherein the combined solution further comprises at least one biologically active agent.

53. The method of claim 29, wherein the self-assembling peptide is one of (RADA)$_p$, wherein p=2-8(SEQ ID NO: 2) and (IEIK)$_p$1, wherein p=2-8(SEQ ID NO: 5).

54. The method of claim 29, wherein the self-assembling peptide is one of (RADA)$_4$ (SEQ ID NO: 10) and (IEIK)$_3$1 (SEQ ID NO: 11).

* * * * *

SEQUENCE LISTING

<160> NUMBER OF SEQ ID NOS: 69

<210> SEQ ID NO 1
<211> LENGTH: 4
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ala Asp Ala
1

<210> SEQ ID NO 2
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (9)..(200)
<223> OTHER INFORMATION: /replace=" "
<220> FEATURE:
<221> NAME/KEY: misc_feature
<222> LOCATION: (1)..(200)
<223> OTHER INFORMATION: /note="This sequence many encompass 2-50 'Arg
      Ala Asp Ala' repeating units"
<220> FEATURE:
<221> NAME/KEY: misc_feature
<222> LOCATION: (1)..(200)
<223> OTHER INFORMATION: /note="Variant residues given in the sequence
      have no preference with respect to those in the annotations for
      variant positions"

<400> SEQUENCE: 2

Arg Ala Asp Ala Arg Ala Asp Ala Arg Ala Asp Ala Arg Ala Asp Ala
1               5                   10                  15

Arg Ala Asp Ala Arg Ala Asp Ala Arg Ala Asp Ala Arg Ala Asp Ala
            20                  25                  30

Arg Ala Asp Ala Arg Ala Asp Ala Arg Ala Asp Ala Arg Ala Asp Ala
        35                  40                  45

Arg Ala Asp Ala Arg Ala Asp Ala Arg Ala Asp Ala Arg Ala Asp Ala
    50                  55                  60

Arg Ala Asp Ala Arg Ala Asp Ala Arg Ala Asp Ala Arg Ala Asp Ala
65                  70                  75                  80

Arg Ala Asp Ala Arg Ala Asp Ala Arg Ala Asp Ala Arg Ala Asp Ala
                85                  90                  95

Arg Ala Asp Ala Arg Ala Asp Ala Arg Ala Asp Ala Arg Ala Asp Ala
            100                 105                 110

Arg Ala Asp Ala Arg Ala Asp Ala Arg Ala Asp Ala Arg Ala Asp Ala
        115                 120                 125

Arg Ala Asp Ala Arg Ala Asp Ala Arg Ala Asp Ala Arg Ala Asp Ala
    130                 135                 140

Arg Ala Asp Ala Arg Ala Asp Ala Arg Ala Asp Ala Arg Ala Asp Ala
145                 150                 155                 160

Arg Ala Asp Ala Arg Ala Asp Ala Arg Ala Asp Ala Arg Ala Asp Ala
                165                 170                 175

Arg Ala Asp Ala Arg Ala Asp Ala Arg Ala Asp Ala Arg Ala Asp Ala
            180                 185                 190

Arg Ala Asp Ala Arg Ala Asp Ala
        195                 200

<210> SEQ ID NO 3
```

```
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ile Glu Ile Lys
1

<210> SEQ ID NO 4
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (9)..(200)
<223> OTHER INFORMATION: /replace=" "
<220> FEATURE:
<221> NAME/KEY: misc_feature
<222> LOCATION: (1)..(200)
<223> OTHER INFORMATION: /note="This sequence many encompass 2-50 'Ile
      Glu Ile Lys' repeating units"
<220> FEATURE:
<221> NAME/KEY: misc_feature
<222> LOCATION: (1)..(200)
<223> OTHER INFORMATION: /note="Variant residues given in the sequence
      have no preference with respect to those in the annotations for
      variant positions"

<400> SEQUENCE: 4

Ile Glu Ile Lys Ile Glu Ile Lys Ile Glu Ile Lys Ile Glu Ile Lys
1               5                   10                  15

Ile Glu Ile Lys Ile Glu Ile Lys Ile Glu Ile Lys Ile Glu Ile Lys
            20                  25                  30

Ile Glu Ile Lys Ile Glu Ile Lys Ile Glu Ile Lys Ile Glu Ile Lys
        35                  40                  45

Ile Glu Ile Lys Ile Glu Ile Lys Ile Glu Ile Lys Ile Glu Ile Lys
    50                  55                  60

Ile Glu Ile Lys Ile Glu Ile Lys Ile Glu Ile Lys Ile Glu Ile Lys
65                  70                  75                  80

Ile Glu Ile Lys Ile Glu Ile Lys Ile Glu Ile Lys Ile Glu Ile Lys
                85                  90                  95

Ile Glu Ile Lys Ile Glu Ile Lys Ile Glu Ile Lys Ile Glu Ile Lys
            100                 105                 110

Ile Glu Ile Lys Ile Glu Ile Lys Ile Glu Ile Lys Ile Glu Ile Lys
        115                 120                 125

Ile Glu Ile Lys Ile Glu Ile Lys Ile Glu Ile Lys Ile Glu Ile Lys
    130                 135                 140

Ile Glu Ile Lys Ile Glu Ile Lys Ile Glu Ile Lys Ile Glu Ile Lys
145                 150                 155                 160

Ile Glu Ile Lys Ile Glu Ile Lys Ile Glu Ile Lys Ile Glu Ile Lys
                165                 170                 175

Ile Glu Ile Lys Ile Glu Ile Lys Ile Glu Ile Lys Ile Glu Ile Lys
            180                 185                 190

Ile Glu Ile Lys Ile Glu Ile Lys
        195                 200
```

```
<210> SEQ ID NO 5
<211> LENGTH: 201
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (9)..(200)
<223> OTHER INFORMATION: /replace=" "
<220> FEATURE:
<221> NAME/KEY: misc_feature
<222> LOCATION: (1)..(201)
<223> OTHER INFORMATION: /note="This sequence many encompass 2-50 'Ile
      Glu Ile Lys' repeating units"
<220> FEATURE:
<221> NAME/KEY: misc_feature
<222> LOCATION: (1)..(201)
<223> OTHER INFORMATION: /note="Variant residues given in the sequence
      have no preference with respect to those in the annotations for
      variant positions"

<400> SEQUENCE: 5

Ile Glu Ile Lys Ile Glu Ile Lys Ile Glu Ile Lys Ile Glu Ile Lys
1               5                   10                  15

Ile Glu Ile Lys Ile Glu Ile Lys Ile Glu Ile Lys Ile Glu Ile Lys
            20                  25                  30

Ile Glu Ile Lys Ile Glu Ile Lys Ile Glu Ile Lys Ile Glu Ile Lys
        35                  40                  45

Ile Glu Ile Lys Ile Glu Ile Lys Ile Glu Ile Lys Ile Glu Ile Lys
    50                  55                  60

Ile Glu Ile Lys Ile Glu Ile Lys Ile Glu Ile Lys Ile Glu Ile Lys
65                  70                  75                  80

Ile Glu Ile Lys Ile Glu Ile Lys Ile Glu Ile Lys Ile Glu Ile Lys
                85                  90                  95

Ile Glu Ile Lys Ile Glu Ile Lys Ile Glu Ile Lys Ile Glu Ile Lys
            100                 105                 110

Ile Glu Ile Lys Ile Glu Ile Lys Ile Glu Ile Lys Ile Glu Ile Lys
        115                 120                 125

Ile Glu Ile Lys Ile Glu Ile Lys Ile Glu Ile Lys Ile Glu Ile Lys
    130                 135                 140

Ile Glu Ile Lys Ile Glu Ile Lys Ile Glu Ile Lys Ile Glu Ile Lys
145                 150                 155                 160

Ile Glu Ile Lys Ile Glu Ile Lys Ile Glu Ile Lys Ile Glu Ile Lys
                165                 170                 175

Ile Glu Ile Lys Ile Glu Ile Lys Ile Glu Ile Lys Ile Glu Ile Lys
            180                 185                 190

Ile Glu Ile Lys Ile Glu Ile Lys Ile
        195                 200

<210> SEQ ID NO 6
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Lys Leu Asp Leu
```

<210> SEQ ID NO 7
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (9)..(200)
<223> OTHER INFORMATION: /replace=" "
<220> FEATURE:
<221> NAME/KEY: misc_feature
<222> LOCATION: (1)..(200)
<223> OTHER INFORMATION: /note="This sequence many encompass 2-50 'Lys Leu Asp Leu' repeating units"
<220> FEATURE:
<221> NAME/KEY: misc_feature
<222> LOCATION: (1)..(200)
<223> OTHER INFORMATION: /note="Variant residues given in the sequence have no preference with respect to those in the annotations for variant positions"

<400> SEQUENCE: 7

Lys Leu Asp Leu Lys Leu Asp Leu Lys Leu Asp Leu Lys Leu Asp Leu
1               5                   10                  15

Lys Leu Asp Leu Lys Leu Asp Leu Lys Leu Asp Leu Lys Leu Asp Leu
            20                  25                  30

Lys Leu Asp Leu Lys Leu Asp Leu Lys Leu Asp Leu Lys Leu Asp Leu
        35                  40                  45

Lys Leu Asp Leu Lys Leu Asp Leu Lys Leu Asp Leu Lys Leu Asp Leu
    50                  55                  60

Lys Leu Asp Leu Lys Leu Asp Leu Lys Leu Asp Leu Lys Leu Asp Leu
65                  70                  75                  80

Lys Leu Asp Leu Lys Leu Asp Leu Lys Leu Asp Leu Lys Leu Asp Leu
                85                  90                  95

Lys Leu Asp Leu Lys Leu Asp Leu Lys Leu Asp Leu Lys Leu Asp Leu
            100                 105                 110

Lys Leu Asp Leu Lys Leu Asp Leu Lys Leu Asp Leu Lys Leu Asp Leu
        115                 120                 125

Lys Leu Asp Leu Lys Leu Asp Leu Lys Leu Asp Leu Lys Leu Asp Leu
    130                 135                 140

Lys Leu Asp Leu Lys Leu Asp Leu Lys Leu Asp Leu Lys Leu Asp Leu
145                 150                 155                 160

Lys Leu Asp Leu Lys Leu Asp Leu Lys Leu Asp Leu Lys Leu Asp Leu
                165                 170                 175

Lys Leu Asp Leu Lys Leu Asp Leu Lys Leu Asp Leu Lys Leu Asp Leu
            180                 185                 190

Lys Leu Asp Leu Lys Leu Asp Leu
        195                 200

<210> SEQ ID NO 8
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Lys Leu Asp
1

<210> SEQ ID NO 9
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (7)..(150)
<223> OTHER INFORMATION: /replace=" "
<220> FEATURE:
<221> NAME/KEY: misc_feature
<222> LOCATION: (1)..(150)
<223> OTHER INFORMATION: /note="This sequence many encompass 2-50 'Lys
      Leu Asp' repeating units"
<220> FEATURE:
<221> NAME/KEY: misc_feature
<222> LOCATION: (1)..(150)
<223> OTHER INFORMATION: /note="Variant residues given in the sequence
      have no preference with respect to those in the annotations for
      variant positions"

<400> SEQUENCE: 9

Lys Leu Asp Lys Leu Asp Lys Leu Asp Lys Leu Asp Lys Leu Asp Lys
1               5                   10                  15

Leu Asp Lys Leu Asp Lys Leu Asp Lys Leu Asp Lys Leu Asp Lys Leu
            20                  25                  30

Asp Lys Leu Asp Lys Leu Asp Lys Leu Asp Lys Leu Asp Lys Leu Asp
        35                  40                  45

Lys Leu Asp Lys Leu Asp Lys Leu Asp Lys Leu Asp Lys Leu Asp Lys
    50                  55                  60

Leu Asp Lys Leu Asp Lys Leu Asp Lys Leu Asp Lys Leu Asp Lys Leu
65                  70                  75                  80

Asp Lys Leu Asp Lys Leu Asp Lys Leu Asp Lys Leu Asp Lys Leu Asp
            85                  90                  95

Lys Leu Asp Lys Leu Asp Lys Leu Asp Lys Leu Asp Lys Leu Asp Lys
            100                 105                 110

Leu Asp Lys Leu Asp Lys Leu Asp Lys Leu Asp Lys Leu Asp Lys Leu
            115                 120                 125

Asp Lys Leu Asp Lys Leu Asp Lys Leu Asp Lys Leu Asp Lys Leu Asp
        130                 135                 140

Lys Leu Asp Lys Leu Asp
145                 150

<210> SEQ ID NO 10
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Arg Ala Asp Ala Arg Ala Asp Ala Arg Ala Asp Ala Arg Ala Asp Ala
1               5                   10                  15

<210> SEQ ID NO 11
<211> LENGTH: 13

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Glu Ile Lys Ile Glu Ile Lys Ile Glu Ile Lys Ile
1               5                   10

<210> SEQ ID NO 12
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ile Glu Ile Lys Ile Glu Ile Lys Ile Glu Ile Lys Ile Glu Ile Lys
1               5                   10                  15

Ile

<210> SEQ ID NO 13
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Lys Leu Asp Leu Lys Leu Asp Leu Lys Leu Asp Leu
1               5                   10

<210> SEQ ID NO 14
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ala Glu Ala Glu Ala Lys Ala Lys Ala Glu Ala Glu Ala Lys Ala Lys
1               5                   10                  15

<210> SEQ ID NO 15
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Lys Ala Lys Ala Lys Ala Lys Ala Lys Ala Lys Ala Lys Ala Lys Ala
1               5                   10                  15

<210> SEQ ID NO 16
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 16

Lys Ala Lys Ala Lys
1               5

<210> SEQ ID NO 17
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ala Lys Ala Lys Ala Glu Ala Glu Ala Lys Ala Lys Ala Glu Ala Glu
1               5                   10                  15

<210> SEQ ID NO 18
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ala Lys Ala Glu Ala Lys Ala Glu Ala Lys Ala Glu Ala Lys Ala Glu
1               5                   10                  15

<210> SEQ ID NO 19
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Glu Ala Lys Ala Glu Ala Lys Ala Glu Ala Lys Ala Glu Ala Lys Ala
1               5                   10                  15

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ala Glu Ala Glu Ala Lys Ala Lys
1               5

<210> SEQ ID NO 21
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 21

Ala Glu Ala Lys Ala Glu Ala Glu Ala Lys Ala Lys
1               5                   10

<210> SEQ ID NO 22
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Lys Ala Glu Ala Lys Ala Glu Ala Lys Ala Glu Ala Lys Ala Glu Ala
1               5                   10                  15

<210> SEQ ID NO 23
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ala Glu Ala Lys Ala Glu Ala Lys Ala Glu Ala Lys Ala Glu Ala Lys
1               5                   10                  15

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ala Arg Ala Arg Ala Asp Ala Asp
1               5

<210> SEQ ID NO 25
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ala Asp Ala Asp Ala Arg Ala Arg Ala Asp Ala Asp Ala Arg Ala Arg
1               5                   10                  15

<210> SEQ ID NO 26
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ala Arg Ala Asp Ala Arg Ala Asp Ala Arg Ala Asp Ala Arg Ala Asp
```

<210> SEQ ID NO 27
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asp Ala Arg Ala Asp Ala Arg Ala Asp Ala Arg Ala Asp Ala Arg Ala
1               5                   10                  15

<210> SEQ ID NO 28
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ala Asp Ala Arg Ala Asp Ala Arg Ala Asp Ala Arg Ala Asp Ala Arg
1               5                   10                  15

<210> SEQ ID NO 29
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ala Arg Ala Arg Ala Asp Ala Asp Ala Arg Ala Arg Ala Asp Ala Asp
1               5                   10                  15

<210> SEQ ID NO 30
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ala Arg Ala Asp Ala Lys Ala Glu Ala Arg Ala Asp Ala Lys Ala Glu
1               5                   10                  15

<210> SEQ ID NO 31
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ala Lys Ala Glu Ala Arg Ala Asp Ala Lys Ala Glu Ala Arg Ala Asp
1               5                   10                  15

<210> SEQ ID NO 32

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ala Arg Ala Lys Ala Asp Ala Glu Ala Arg Ala Lys Ala Asp Ala Glu
1               5                   10                  15

<210> SEQ ID NO 33
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ala Lys Ala Arg Ala Glu Ala Asp Ala Lys Ala Arg Ala Asp Ala Glu
1               5                   10                  15

<210> SEQ ID NO 34
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Gln Ala Gln Ala Gln Ala Gln Ala Gln Ala Gln Ala Gln Ala Gln
1               5                   10                  15

<210> SEQ ID NO 35
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Val Gln Val Gln Val Gln Val Gln Val Gln Val Gln Val Gln Val Gln
1               5                   10                  15

<210> SEQ ID NO 36
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Tyr Gln Tyr Gln Tyr Gln Tyr Gln Tyr Gln Tyr Gln Tyr Gln Tyr Gln
1               5                   10                  15

<210> SEQ ID NO 37
<211> LENGTH: 16
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 37

His Gln His Gln His Gln His Gln His Gln His Gln His Gln His Gln
1               5                   10                  15

<210> SEQ ID NO 38
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Asn Ala Asn Ala Asn Ala Asn Ala Asn Ala Asn Ala Asn Ala Asn
1               5                   10                  15

<210> SEQ ID NO 39
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Val Asn Val Asn Val Asn Val Asn Val Asn Val Asn Val Asn Val Asn
1               5                   10                  15

<210> SEQ ID NO 40
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Tyr Asn Tyr Asn Tyr Asn Tyr Asn Tyr Asn Tyr Asn Tyr Asn Tyr Asn
1               5                   10                  15

<210> SEQ ID NO 41
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

His Asn His Asn His Asn His Asn His Asn His Asn His Asn His Asn
1               5                   10                  15

<210> SEQ ID NO 42
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 42

Ala Asn Ala Gln Ala Asn Ala Gln Ala Asn Ala Gln Ala Asn Ala Gln
1               5                   10                  15

<210> SEQ ID NO 43
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ala Gln Ala Asn Ala Gln Ala Asn Ala Gln Ala Asn Ala Gln Ala Asn
1               5                   10                  15

<210> SEQ ID NO 44
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Val Asn Val Gln Val Asn Val Gln Val Asn Val Gln Val Asn Val Gln
1               5                   10                  15

<210> SEQ ID NO 45
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Val Gln Val Asn Val Gln Val Asn Val Gln Val Asn Val Gln Val Asn
1               5                   10                  15

<210> SEQ ID NO 46
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Tyr Asn Tyr Gln Tyr Asn Tyr Gln Tyr Asn Tyr Gln Tyr Asn Tyr Gln
1               5                   10                  15

<210> SEQ ID NO 47
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Tyr Gln Tyr Asn Tyr Gln Tyr Asn Tyr Gln Tyr Asn Tyr Gln Tyr Asn
1               5                   10                  15
```

```
<210> SEQ ID NO 48
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

His Asn His Gln His Asn His Gln His Asn His Gln His Asn His Gln
1               5                   10                  15

<210> SEQ ID NO 49
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

His Gln His Asn His Gln His Asn His Gln His Asn His Gln His Asn
1               5                   10                  15

<210> SEQ ID NO 50
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ala Lys Ala Gln Ala Asp Ala Lys Ala Gln Ala Asp Ala Lys Ala Gln
1               5                   10                  15

Ala Asp

<210> SEQ ID NO 51
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Val Lys Val Gln Val Asp Val Lys Val Gln Val Asp Val Lys Val Gln
1               5                   10                  15

Val Asp

<210> SEQ ID NO 52
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Tyr Lys Tyr Gln Tyr Asp Tyr Lys Tyr Gln Tyr Asp Tyr Lys Tyr Gln
1               5                   10                  15
```

Tyr Asp

```
<210> SEQ ID NO 53
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53
```

His Lys His Gln His Asp His Lys His Gln His Asp His Lys His Gln
1               5                   10                  15

His Asp

```
<210> SEQ ID NO 54
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54
```

Ala Thr Ala Thr
1

```
<210> SEQ ID NO 55
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55
```

Thr Val Thr Val
1

```
<210> SEQ ID NO 56
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56
```

Ala Ser Ala Ser
1

```
<210> SEQ ID NO 57
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57
```

Ser Ser Ser Ser
1

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Val Val Val Thr Thr Thr Thr
1               5

<210> SEQ ID NO 59
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Arg Ala Asp
1

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ala Ala Ala Ala Ala Ala Lys
1               5

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ala Ala Ala Ala Ala Ala Asp
1               5

<210> SEQ ID NO 62
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ala Thr Ala Thr Ala Thr Ala Thr
1               5

<210> SEQ ID NO 63
<211> LENGTH: 8

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Thr Val Thr Val Thr Val Thr Val
1               5

<210> SEQ ID NO 64
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ala Ser Ala Ser Ala Ser Ala Ser
1               5

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ser Ser Ser Ser Ser Ser Ser
1               5

<210> SEQ ID NO 66
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Val Arg Val Arg Val Asp Val Asp Val Arg Val Arg Val Asp Val Asp
1               5                   10                  15

<210> SEQ ID NO 67
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ala Asp Ala Asp Ala Lys Ala Lys Ala Asp Ala Asp Ala Lys Ala Lys
1               5                   10                  15

<210> SEQ ID NO 68
<211> LENGTH: 16
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 68

Glu Ala Glu Ala Glu Ala Glu Ala Glu Ala Glu Ala Glu Ala Glu Ala
1               5                   10                  15

<210> SEQ ID NO 69
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Ala Asp Ala Asp Ala Asp Ala Asp Ala Asp Ala Asp Ala Asp Ala Asp
1               5                   10                  15
```